United States Patent [19]

Chang et al.

[11] Patent Number: 5,120,528

[45] Date of Patent: Jun. 9, 1992

[54] TASTE PRESERVING, MILD ORAL HYGIENE COMPOSITIONS

[75] Inventors: Tiang-shing Chang, Westfield, N.J.; Joseph Kanapka, Briancliff Manor, N.Y.; Michael C. Alfano, Franklin Lakes, N.J.

[73] Assignee: Block Drug Company, Inc., Jersey City, N.J.

[21] Appl. No.: 713,512

[22] Filed: Jun. 12, 1991

[51] Int. Cl.$^5$ .......................... A61K 7/16; A61K 7/18
[52] U.S. Cl. .................................. 424/49; 424/52
[58] Field of Search ...................... 424/49-58

[56] References Cited

U.S. PATENT DOCUMENTS

| | | | |
|---|---|---|---|
| 3,873,721 | 3/1975 | Hargett | 424/49 |
| 3,897,548 | 7/1975 | Katz | 424/54 |
| 3,942,512 | 3/1976 | Hargett | 424/49 |
| 3,971,852 | 7/1976 | Brenner et al. | 424/49 |
| 3,975,514 | 8/1976 | Weissz | 424/52 |
| 4,115,313 | 9/1978 | Lyon | 424/49 |
| 4,269,822 | 5/1981 | Pellico et al. | 424/55 |
| 4,376,781 | 3/1983 | Lietti et al. | 514/927 |
| 4,391,798 | 7/1983 | Tavss et al. | 424/52 |
| 4,419,346 | 12/1983 | Stroz et al. | 424/151 |
| 4,428,930 | 1/1984 | Chang | 424/52 |
| 4,470,964 | 9/1984 | Chang | 424/52 |
| 4,725,576 | 2/1988 | Pollock et al. | 514/2 |
| 4,828,824 | 5/1989 | Grollier | 424/52 |
| 4,835,002 | 5/1989 | Wolf et al. | 426/590 |
| 4,863,900 | 9/1989 | Pollock et al. | 514/12 |
| 4,868,287 | 9/1989 | Sikes et al. | 530/324 |
| 4,942,034 | 7/1990 | Hill et al. | 424/401 |
| 4,950,479 | 8/1990 | Hill et al. | 424/49 |
| 4,983,404 | 1/1991 | Raman et al. | 426/650 |

FOREIGN PATENT DOCUMENTS

| | | |
|---|---|---|
| 180483 | 5/1986 | European Pat. Off. . |
| 256821 | 2/1988 | European Pat. Off. . |
| 3417235 | 6/1985 | Fed. Rep. of Germany . |
| 3627296 | 2/1988 | Fed. Rep. of Germany . |

Primary Examiner—Shep K. Rose
Attorney, Agent, or Firm—Ostrolenk, Faber, Gerb & Soffen

[57] ABSTRACT

This invention relates to a mild oral hygiene composition such as a toothpaste, dental gel, mouthrinse or tooth powder containing a mild surfactant, protein fatty acid condensate or acid hydrolyzed, hydrolyzed animal protein or the mixtures thereof, and in combination therewith, mild high foaming surfactant, e.g., disodium cocoamido MIPA sulfosuccinate or disodium oleamido PEG-2 sulfosuccinate or disodium lauryl sulfosuccinate or the mixtures thereof; or a natural emulsifier, e.g., lecithin, or both a mild surfactant and a nautral emulsifier.

16 Claims, No Drawings

TASTE PRESERVING, MILD ORAL HYGIENE COMPOSITIONS

BACKGROUND OF THE INVENTION

The surfactant in dental hygiene products serves many purposes They are used for their detersive, emulsifying and antimicrobial properties in addition to their foaming character Many consumers believe that high foam and rapid break-up indicate a superior cleaning ability.

The most commonly used surfactant in marketed dentifrices is sodium lauryl sulfate. It is readily available at low cost and generates a high foam. However, inclusion of this detergent in a dentifrice formulation requires the addition of high levels of costly flavor oils to mask the bitter taste of sodium lauryl sulfate itself.

Sodium lauryl sulfate also has been accused of generating a so called "orange juice effect". This effect may be detected as an unpleasant residual flavor note left in the mouth following the ingestion of orange juice after toothbrushing with a toothpaste containing the sodium lauryl sulfate Indeed, in psychophysical evaluation of the effect of sodium lauryl sulfate on the taste of citric acid, it was determined that the surfactant added a distinctly bitter component to the usual sour taste of citric acid In addition, it is also known that sodium lauryl sulfate and flavor oils are severe dermal irritants. Therefore, it would be advantageous to replace sodium lauryl sulfate with a surfactant or a combination of surfactants, which possess a mild taste, a low dermal irritation potential and foaming properties comparable to the oral composition containing sodium lauryl sulfate. Furthermore, the flavor oils level for this mild tasting dentifrice could be lowered significantly and thereby further reduce the dermal irritation potential of the oral composition and eliminate the so called "orange juice effect".

SUMMARY OF THE INVENTION

In accordance with this invention, improved oral hygiene compositions in the forms of dentifrice pastes, gels, powders and mouthrinses are provided These compositions contain in an oral hygiene, e.g. dental, vehicle, a protein derivative which may be a protein fatty acid condensate or an acid hydrolyzed animal protein, and at least one high foaming mild surfactant such as a sulfosuccinate and a natural emulsifier, e.g., lecithin Suitably, the protein fatty acid condensate is potassium coco-hydrolyzed collagen or triethanolamine coco-hydrolyzed collagen acid and the acid hydrolyzed animal protein is collagen peptide; and the high foaming mild surfactant is suitably disodium oleamido PEG-2 sulfosuccinate, disodium cocoamido MIPA sulfosuccinate or disodium lauryl sulfosuccinate or mixtures thereof When the composition does not contain lecithin, a flavor oil is incorporated. In compositions containing lecithin, a flavor oil may optionally be included Lecithin, in addition to enhancing the dispersion of the flavor oil, improves the flavor impact in the oral environment.

The preferred compositions of this invention suitably comprise

A) from about 0 01% to about 4 00% of a mild surfactant, a protein fatty acid condensate having an average molecular weight from about 650 to about 900 or an acid hydrolyzed animal protein having an average molecular weight from about 500 to about 2000 or mixtures thereof;

B) from about 0.01% to about 1.5% of a high foaming mild surfactant, e.g., a sulfosuccinate C) from about 0 01% to about 5.00% of a natural emulsifier, lecithin, to enhance the dispersion of the flavor oils in the dentifrice and to improve the flavor impact in the oral cavity;

D) from 0 to about 1.0%, preferably from about 0.01 to 1.0%, and most preferably, from 0.01 to 0.45% of a flavor oil.

All percentages given are percentages by weight of the fully compounded oral composition The compositions contemplated include toothpastes and dental gels wherein the preferred protein derivatives are potassium coco-hydrolyzed collagen, triethanolamine coco-hydrolyzed collagen and acid hydrolyzed collagen peptide, and the preferred high foaming sulfosuccinates are disodium oleamido PEG-2 sulfosuccinate and disodium cocoamido MIPH sulfosuccinate; toothpowders wherein the preferred protein derivative is collagen peptide and the preferred high foaming sulfosuccinate is disodium lauryl sulfosuccinate; and mouthrinses wherein the preferred protein derivative are potassium cocohydrolyzed collagen and triethanolamine coco-hydrolyzed collagen Also contemplated are toothpastes containing polyoxyethylene (40) stearate as a foam stabilizer.

DESCRIPTION OF THE PREFERRED EMBODIMENTS

The preferred mild oral hygiene compositions of this invention, such as toothpaste, dental gels, toothpowders, and mouthrinses comprise a mild surfactant system and a natural emulsifier, e.g., lecithin. The mild surfactant system contains at least one protein fatty acid condensate or one acid hydrolyzed animal protein or mixtures thereof, from about 0.01% to about 4 0% by weight, optionally, in combination with a sulfosuccinate surfactant, from about 0.01% to about 1.5% by weight, to improve the foam density.

The protein fatty acid condensates are considered to be anionic surfactants having an average molecular weight from about 650 to about 900 and having a general chemical formula:

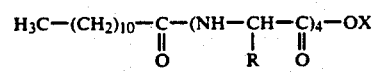

R: Amino acid side chain of collagen
X: Potassium, or triethanolamine

The acid hydrolyzed animal proteins are considered to be cationic surfactants preferred as an acid hydrolyzed collagen having an average molecular weight from about 500 to about 2000 and having a general chemical formula:

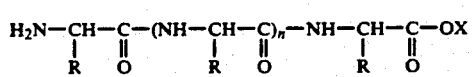

R: Amino acid side chain of collagen
X: Hydrogen, sodium
n=8-11

The sulfosuccinate surfactants are disodium oleamido PEG-2 sulfosuccinate, disodium cocamido MIPA sulfosuccinate and disodium lauryl sulfosuccinate having the general formula:

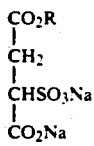

R: Fatty alcohol, ethoxylated fatty alcohol or fatty alkanolamide

The total amount of the mild surfactant system referred to above in the oral composition herein is from about 0.02% to about 5.50% by weight of the said oral composition, preferably, in the range of 0.5% to 3.5%. When a sulfosuccinate surfactant is incorporated into the oral composition to increase the foam density, the ratio of the hydrolyzed animal protein and sulfosuccinate surfactant should be in the range of 0.01 to 20, preferably in the range of 0.1 to 15.

The emulsifier employed according to this invention as an optional component in dispersing flavor oils in the oral composition is preferably soybean lecithin, a natural emulsifier, having an approximate HLB of 7 and a chemical formula:

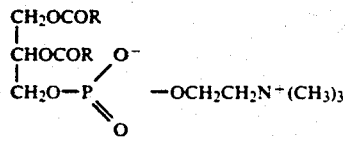

R: Hydrogen or alkyl group

The amount of lecithin referred to above in the oral composition is suitably from about 0 01% to about 5.00% by weight of the said oral composition, preferably, from about 0.10% to about 2.00%.

Other ingredients commonly used in typical dentifrice compositions may include, but are not limited to, water, humectants, sweeteners, colors, opacifiers, abrasives, preservatives, thickeners and pharmacologically active ingredients such as water soluble fluoride, plaque and calculus inhibitors, antimicrobial agents, and desensitizing compounds The sources of fluoride ions are well known in the art as anticaries agents. They are inorganic fluoride salts, such as sodium fluoride, stannous fluoride, sodium monofluorophosphate and the mixtures thereof. The amount of fluoride compounds, generally is from about 0.005% to about 3.00%, which releases from about 50 to about 3000 ppm of fluoride ion by weight of the oral composition.

The liquid vehicle of the dentifrice pastes or gels may comprise water, humectants and thickening agents, in the amount from about 20.0% to about 90.0% by weight of the said composition. Examples of the suitable humectants are glycerine, sorbitol, propylene glycol, polyethylene glycol and the mixtures thereof Examples of suitable thickening agents are modified cellulose products such as sodium carboxymethyl cellulose, hydroxyethyl cellulose, methyl cellulose, etc., and inorganic gel forming ingredients such as silica precipitates, colloidal magnesium aluminum carrageenan, alginates, etc. also are useful thickening agents.

The amount of the abrasive or polishing agents in dentifrices is generally from about 15.0% to about 98.0% by weight of the oral composition, preferably from about 15.0% to about 80.0% in paste and gel and from about 65.0% to about 98.0% in toothpowder Examples of these materials are water-insoluble sodium metaphosphate, potassium metaphosphate, disbasic calcium phosphate anhydrous, dibasic calcium phosphate dihydrate, calcium carbonate, hydrated alumina, etc. In clear gels, the preferred abrasive agents are colloidal silica and alkali metal alumino-silicate since they have refractive indices close to the refractive indices of the liquid gelling agents.

Typical flavor oils suitable for this invention include peppermint, spearmint, cinnamon, anethole, vanilla, lemon, orange and the like, at the levels from about 0.01% to about 1.0%. It is the particular feature of the invention that the flavor oil level for this mild tasting oral composition is significantly lower than the flavor levels in other typical oral compositions containing sodium lauryl sulfate.

In order to achieve cosmetically acceptable dentifrices gels and pastes, it is also useful to incorporate a colorant and a preservative The following examples further describe and provide preferred embodiments within the teachings of the invention and are solely for the purpose of illustration and are not to be considered as limitation of this invention.

EXAMPLES I-III

The following are dental gels of the present invention.

| Ingredient | Weight (%) | | |
| --- | --- | --- | --- |
| | I | II | III |
| Water | 12.51 | 12.51 | 13.41 |
| Glycerine | 10.00 | 10.00 | 10.00 |
| Sorbitol (70%) | 43.00 | 43.00 | 43.00 |
| Sodium carboxymethyl celulose | 0.90 | 0.90 | 0.90 |
| Sodium fluoride | 0.24 | 0.24 | 0.24 |
| Hydrated silica | 30.00 | 30.00 | 30.00 |
| Potassium coco-hydrolyzed collagen (40%) | 1.50 | | |
| Triethanolamine coco-hydrolyzed collagen (40%) | | 1.50 | |
| Collagen peptide | | | 0.80 |
| Disodium oleamido PEG-2 sulfosuccinate | 0.20 | | |
| Disodium cocoamido MIPA sulfosuccinate | | 0.20 | |
| Lecithin | 0.40 | 0.40 | 0.40 |
| Sodium saccharin | 0.15 | 0.15 | 0.15 |
| Methyl paraben | 0.20 | 0.20 | 0.20 |
| Dye solution (1.0%) | 0.70 | 0.70 | 0.70 |
| Flavor | 0.20 | 0.20 | 0.20 |

EXAMPLES IV-VI

The following are toothpastes representative of the present invention.

| Ingredient | Weight (%) | | |
| --- | --- | --- | --- |
| | IV | V | VI |
| Water | 24.85 | 24.90 | 24.85 |
| Glycerine | 16.00 | 16.00 | 16.00 |
| Sorbitol (70%) | 16.00 | 16.00 | 16.00 |
| Natrosol | 1.35 | 1.30 | 1.30 |
| Sodium monofluorophosphate | 0.80 | 0.80 | 0.80 |
| Dicalcium phosphate anhydrous | 7.00 | 7.00 | 7.00 |
| Dicalcium phosphate dihydrate | 30.00 | 30.00 | 30.00 |
| | 30.00 | 30.00 | 30.00 |
| Aerosil | 0.70 | 0.70 | |
| Potassium coco-hydrolyzed | 1.50 | | 1.50 |

-continued

| Ingredient | Weight (%) | | |
|---|---|---|---|
| | IV | V | VI |
| collagen (40%) | | | |
| Triethanolamine coco-collagen peptide (40%) | | 1.50 | |
| Disodium lauryl sulfosuccinate | | | 0.20 |
| Disodium oleamido PEG-2 sulfosuccinate | 0.20 | | |
| Disodium cocoamido MIPA sulfosuccinate | | 0.20 | |
| Lecithin | 0.40 | 0.40 | 0.50 |
| Sodium saccharin | 0.20 | 0.20 | 0.15 |
| Methyl paraben | 0.20 | 0.20 | 0.20 |
| Dye solution (1.0%) | 0.60 | 0.60 | 0.60 |
| Flavor | 0.20 | 0.20 | 0.20 |

EXAMPLES VII-VIII

The following are toothpowders of the present invention.

| Ingredient | Weight (%) | |
|---|---|---|
| | VII | VIII |
| Sodium monofluorophosphate | 0.80 | 0.80 |
| Collagen peptide | 1.00 | 0.80 |
| Disodium lauryl sulfosuccinate | | 0.20 |
| Hydrated silica | 64.00 | 64.00 |
| Dicalcium phosphate dihydrate | 33.70 | |
| Calcium carbonate | | 33.65 |
| Methyl paraben | 0.15 | 0.15 |
| Sodium saccharin | 0.15 | 0.20 |
| Flavor | 0.20 | 0.20 |

EXAMPLES IX-X

The following are mouthrinses of the present invention.

| Ingredient | Weight (%) | |
|---|---|---|
| | IX | X |
| Ethyl alcohol | 5.00 | 7.00 |
| Flavor | 0.10 | 0.10 |
| Glycerine | 18.00 | 15.00 |
| Potassium coco-hydrolyzed collagen | 0.50 | |
| Triethanolamine coco-hydrolyzed collagen | | 0.70 |
| Lecithin | 0.10 | 0.10 |
| Sodium fluoride | 0.02 | 0.02 |
| Dye solution (1.0%) | 0.10 | 0.10 |
| Sodium benzoate | 0.10 | 0.10 |
| Water | 76.03 | 76.88 |

EXAMPLES XI-XII

The following are further examples of toothpastes of the present invention.

| Ingredient | Weight (%) | |
|---|---|---|
| | XI | XII |
| Water, deionized | 27.89 to 27.49 | 42.59 to 43.09 |
| Sodium fluoride | 0.24 | 0.24 |
| Methylparaben | 0.12 | 0.12 |
| Propylparaben | 0.05 | 0.05 |
| Sodium saccharin | 0.30 | 0.20 |
| Titanium dioxide | 1.00 | 1.00 |
| Polyoxyethylene (40) stearate | 2.00 | 2.00 |
| Fumed silica | 0.60 | 1.20 |
| Sorbitol 70% aqueous solution | 12.00 | 12.00 |
| Amorphous silica gel | 26.00 | 14.00 |
| Glycerin | 25.00 | 10.00 |
| Guar gum | 0.40 | 0.40 |
| Sodium carboxymethylcellulose | 1.40 | 1.70 |
| Potassium Coco-hydrolyzed animal protein | 2.00 | 1.50 |
| Flavor | 0.60 to 1.00 | 0.2 to 0.7 |
| Lecithin powder | 0.30 | 0.30 |
| Disodium lauryl sulfosuccinate | 0.10 | — |

While certain representative embodiments and details have been shown for the purpose of illustrating the invention, it will be apparent to those skilled in the art that various changes may be made therein without departing from the spirit or scope of the invention.

What is claimed is:

1. An oral hygiene composition which is free of sodium lauryl sulfate, comprising a protein derivative selected from the group consisting of protein fatty acid condensates and acid hydrolyzed animal proteins, together with a flavor oil, a high foaming sulfosuccinate and a natural emulsifier, wherein said protein derivative is present in an amount of about 0.01 to 4.00% by weight, said high foaming sulfosuccinate is present in an amount of about 0.01 to 1.50% by weight, said natural emulsifier is lecithin, said lecithin being present in an amount of about 0.01 to 5.00% by weight, and said flavor oil is present in an amount of about 0.01 to 1.0% by weight and which further contains from about 0.005% to about 3.00% by weight of a fluoride anticaries agent.

2. An oral hygiene composition according to claim 1 wherein said natural emulsifier is lecithin.

3. An oral hygiene composition according to claim 1 wherein said flavor oil is present in an amount of about 0.01 to 0.45% by weight.

4. An oral hygiene composition according to claim 1, said composition being in the form of toothpaste or a dental gel, wherein said protein derivative is a member of the group consisting of potassium coco-hydrolyzed collagen, triethanolamine coco-hydrolyzed collagen, potassium coco-hydrolyzed animal protein and collagen peptide.

5. An oral hygiene composition according to claim 1, said composition being in the form of a toothpaste or a dental gel, wherein said high foaming sulfosuccinate is selected from the group consisting of disodium oleamido PEG-2 sulfosuccinate and disodium cocoamido MIPA sulfosuccinate.

6. An oral hygiene composition which is free of sodium lauryl sulfate, comprising a protein derivative selected from the group consisting of protein fatty acid condensates and acid hydrolyzed animal proteins, together with a flavor oil and a high foaming sulfosuccinate, wherein said protein derivative is present in an amount of about 0.01 to 4.00% by weight, said high foaming sulfosuccinate is present in an amount of about 0.01 to 1.50% by weight and said flavor oil is present in an amount of about 0.01 to 1.0% by weight and which further contains from about 0.005% to about 3.00% by weight of a fluoride anticaries agent.

7. An oral hygiene composition according to claim 6, said composition being in the form of a toothpowder, wherein said protein derivative is collagen peptide.

8. An oral hygiene composition according to claim 6, said composition being in the form of a toothpowder, wherein said high foaming sulfosuccinate is disodium lauryl sulfosuccinate.

9. An oral hygiene composition which is free of sodium lauryl sulfate, comprising a protein derivative selected from the group consisting of protein fatty acid condensates and acid hydrolyzed animal proteins, together with a natural emulsifier, wherein said protein derivative is present in an amount of about 0.01 to about 4.00% by weight, said natural emulsifier is lecithin, said lecithin being present in an amount of about 0.01 to about 5.00% by weight, the composition further containing from about 0.005 to about 3.00% by weight of a fluoride anticaries agent.

10. An oral hygiene composition according to claim 9 wherein said natural emulsifier is lecithin.

11. An oral hygiene composition according to claim 10 in the form of a toothpaste and wherein said protein derivative is potassium coco-hydrolyzed animal protein.

12. An oral hygiene composition according to claim 9 containing also a flavor oil.

13. An oral hygiene composition according to claim 12, wherein said flavor oil is present in an amount of about 0.01 to 1.0% by weight.

14. An oral hygiene composition according to claim 13 wherein said flavor oil is present in an amount of about 0.01 to 0.45% by weight.

15. An oral hygiene composition according to claim 9 in the form of a toothpaste, said composition also comprising polyoxyethylene (40) stearate.

16. An oral hygiene composition according to claim 10 in the form of a mouthrinse, wherein said protein derivative is selected from the group consisting of potassium coco-hydrolyzed collagen and triethanolamine coco-hydrolyzed collagen.

* * * * *